United States Patent
Pawlik et al.

(10) Patent No.: US 8,937,712 B2
(45) Date of Patent: *Jan. 20, 2015

(54) AUTHENTICATION DEVICE WITH ACCESS CONTROL AND CALIBRATION

(75) Inventors: Thomas D. Pawlik, Rochester, NY (US); Myra T. Olm, Webster, NY (US); Thomas J. Widzinski, Rochester, NY (US); Judith A. Bose, Webster, NY (US); Mark P. Henry, Rush, NY (US)

(73) Assignee: Eastman Kodak Company, Rochester, NY (US)

( * ) Notice: Subject to any disclaimer, the term of this patent is extended or adjusted under 35 U.S.C. 154(b) by 265 days.

This patent is subject to a terminal disclaimer.

(21) Appl. No.: 13/587,119

(22) Filed: Aug. 16, 2012

(65) Prior Publication Data

US 2014/0048723 A1 Feb. 20, 2014

(51) Int. Cl.
*G06K 9/74* (2006.01)
*G07C 9/00* (2006.01)

(52) U.S. Cl.
CPC ... *G06K 9/74* (2013.01); *G07C 9/00* (2013.01)
USPC .............................................. 356/71; 356/388

(58) Field of Classification Search
CPC .................................. G01N 21/64; G06K 9/74
USPC .............. 356/388–394, 71; 340/5.8; 235/379, 235/454; 250/459.1, 458.1, 302
See application file for complete search history.

(56) References Cited

U.S. PATENT DOCUMENTS

| | | | |
|---|---|---|---|
| 6,603,871 B2 | 8/2003 | Liang | |
| 6,707,539 B2 | 3/2004 | Selinfreund et al. | |
| 7,434,063 B2 | 10/2008 | Watanabe | |
| 7,552,864 B2 | 6/2009 | Weilacher et al. | |
| 7,831,996 B2 | 11/2010 | Dholakia et al. | |
| 8,006,083 B2 | 8/2011 | Sakakibara | |
| 8,006,898 B2 * | 8/2011 | Reinisch et al. | 235/379 |
| 8,153,984 B2 * | 4/2012 | Olm et al. | 250/367 |
| 8,330,122 B2 * | 12/2012 | Smith et al. | 250/458.1 |
| 8,619,245 B1 * | 12/2013 | Pawlik et al. | 356/71 |
| 2012/0275640 A1 * | 11/2012 | Widzinski et al. | 382/100 |
| 2012/0313749 A1 * | 12/2012 | Pawlik et al. | 340/5.8 |

* cited by examiner

*Primary Examiner* — Sang Nguyen
(74) *Attorney, Agent, or Firm* — Nelson Adrian Blish

(57) ABSTRACT

A method of enabling an authenticating device (10) includes providing an enabling target (17); measuring one or more attributes of the enabling target with the authenticating device; comparing at least one measured attribute with a predetermined expected value; enabling the authenticating device when the at least one measured attribute matches the predetermined expected value; and operating the authenticating device.

19 Claims, 4 Drawing Sheets

AUTHENTICATION DEVICE WITH ACCESS CONTROL AND CALIBRATION

CROSS REFERENCE TO RELATED APPLICATIONS

Reference is made to commonly-assigned U.S. patent application Ser. No. 13/587,139 (now U.S. Pat. No. 8,619,245), filed Aug. 16, 2012, entitled AUTHENTICATION DEVICE WITH ACCESS CONTROL AND CALIBRATION, by Pawlik et al.; the disclosure of which is incorporated herein.

FIELD OF THE INVENTION

This invention relates to authentication of items.

BACKGROUND OF THE INVENTION

Marker plus reader-based authentication systems can be used to distinguish authentic from counterfeit items. The authentication is based on the presence of secret markers in the authentic item and the detection of those markers with special readers. The reader responds by giving a pass/fail indication. It is important that the reader (authenticator) does not fall into unauthorized possession, because its pass/fail functionality can be exploited to manufacture a replicated security feature on the counterfeit item.

It is therefore useful to have a means of enabling the authenticator that cannot be realized by possessing the authenticator alone. Such an enabling device could be, for example, a key. However, the corresponding lock on the authentication device could give away this security mechanism and the counterfeiter would attempt to disable the lock mechanism.

It is desirable to have an enabling device to activate the authenticator separate from the authenticator itself. It is also desirable that possession of the authenticator does not make the need for an enabling device readily apparent.

SUMMARY OF THE INVENTION

Briefly, according to one aspect of the present invention a method of enabling an authenticating device includes providing an enabling target; measuring one or more attributes of the enabling target with the authenticating device; comparing at least one measured attribute with a predetermined expected value; enabling the authenticating device when at least one measured attribute matches the predetermined expected value; and operating the authenticating device.

In one embodiment, an "enabling" target is a coating containing the markers that the authenticator can detect in a predetermined composition. Upon powering on the authenticator, it conducts a series of optical measurements to detect the composition of the marker components. Only if the response is within a tolerance band centered on expected values will the authenticator switch its operating mode to pass/fail authentication. It will continue in that mode until the power is removed or a time interval is exceeded. If the responses of the enabling device are outside the tolerance intervals, the authentication will return to an idle or off mode.

The authenticators and enabling targets should be kept under separate custody. If the authenticator is stolen, it will not function without the enabling target. The necessity of an enabling target is inconspicuous because it is not requested by any authenticator response.

In another embodiment the enabling target provides a calibration measurement. If the response falls within the tolerance band, but is slightly below or above the expected value, the operator notes the discrepancy as a change in system performance and alters the detection algorithm by introducing a calibration factor derived from the difference of measured and expected response values. The newly derived calibration factor reduces the variance of the responses of authentic items with respect to their expected response values. This allows for tighter tolerance bands for item authentication, which is valuable for distinguishing authentic from counterfeit items.

The invention and its objects and advantages will become more apparent in the detailed description of the preferred embodiment presented below.

DETAILED DESCRIPTION OF THE INVENTION

The present invention will be directed in particular to elements forming part of, or in cooperation more directly with the apparatus in accordance with the present invention. It is to be understood that elements not specifically shown or described may take various forms well known to those skilled in the art.

Figure 1:
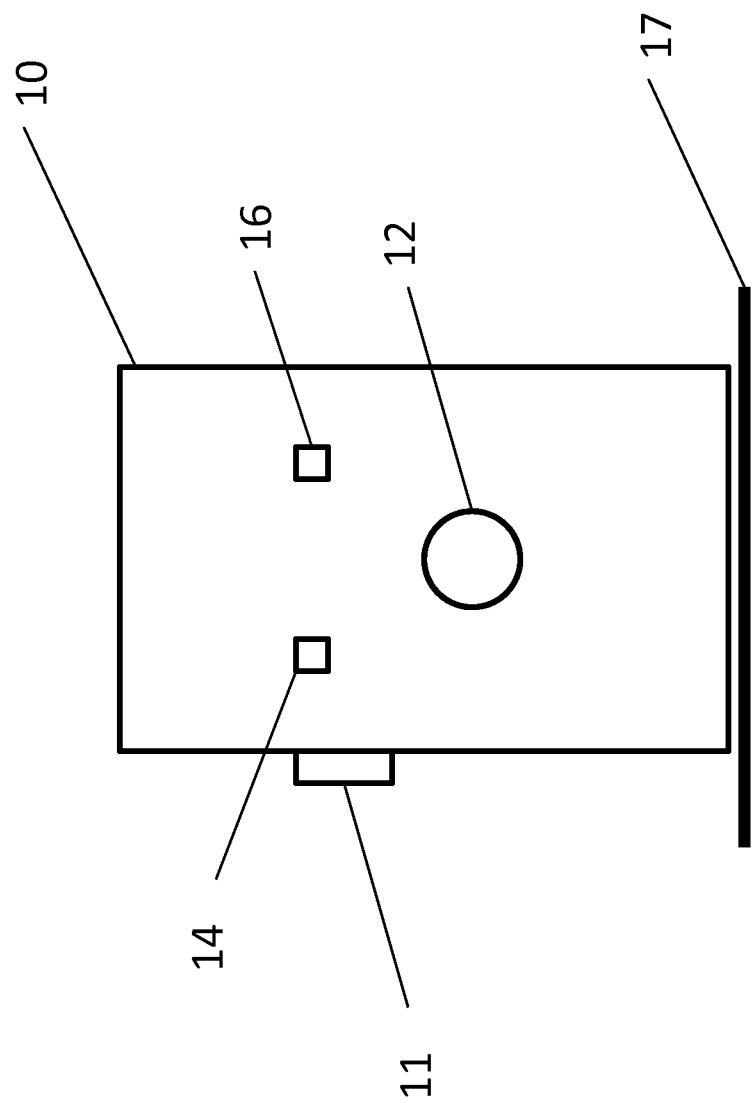
FIG. 1 is a schematic of an authenticating device and an enabling target.

Referring now to FIG. 1 which shows a security marker detection device 10 which can be used to detect emission of security marker materials. FIG. 1 also shows enabling target 17. Upon powering up the device 10 using on/off switch 11 the device cycles through a sequence of optical measurements, discussed in more detail below. By comparing the results of the measurements with data stored in memory 30, shown in FIG. 3, the device determines whether the one or more attributes are present in the enabling target. If the measured attributes are present in the enabling target, the device switches to normal authentication mode wherein a pass/fail authentication of item is initiated by the test button 12.

If the enabling target is not detected, that is, the measured attributes of the enabling target do not match an expected predetermined value, upon power up, the device will be put into a disabled mode where no authentication can be performed. This can, for example, be achieved by disabling the function of the test button 12.

Because of gradual aging of components, external factors and general measurement variability, the results of the measurements of the enabling target will not always exactly match the stored values. The variance can be a sign of degradation of the optical and electrical components of the sensing system. The device can compensate for these factors by calculating one or more calibration factors that can be used to mathematically regenerate the measurement results of a non-degraded system. The calibration factors are then also used to correct the responses in the pass/fail authentication processes. Using this calibration approach, the authentication device can be operated with narrow pass bands and therefore high selectivity while still maintaining robust authentication.

Figure 2:
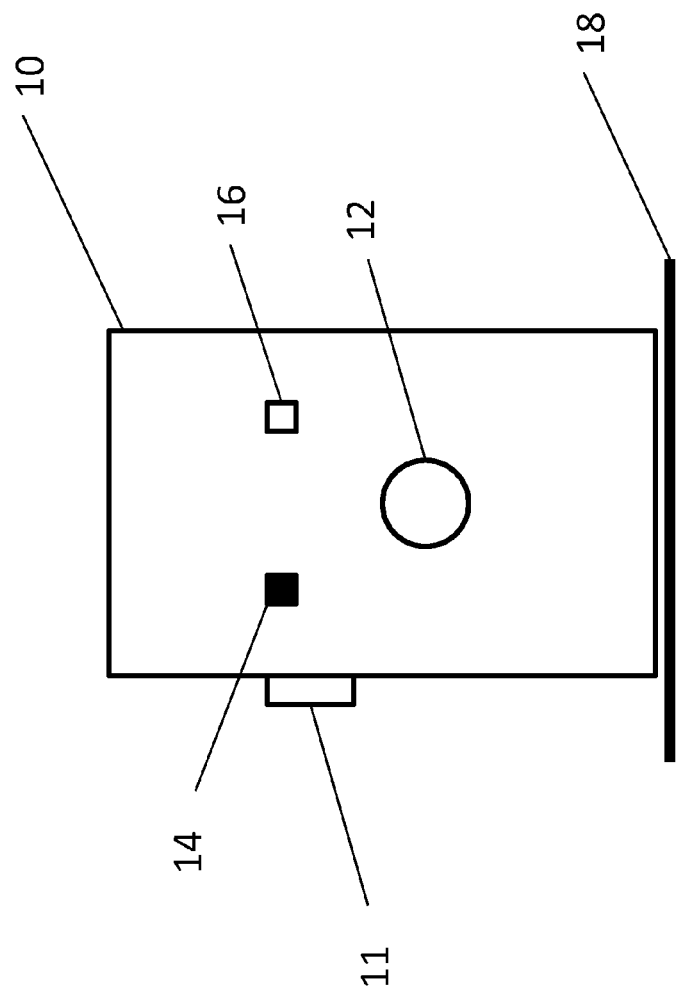
FIG. 2 is a schematic of an authenticating device and authentic item.

Referring now to FIG. 2, the security marker detection system of FIG. 1 is shown, but with an item to be authenticated 18. Authentication is performed by pressing the test button 12. If the item is authentic the pass indicator light 14 will illuminate. If it is not authentic the fail indicator light 16 will light. Authentication of an item or a product is similar to the process used for the enabling target; the authentication device 10 emits electromagnetic radiation 24, shown in FIG. 3, which causes security marker particles in the authenticate article to emit radiation as fluorescence or phosphorescence. The emitted radiation is detected by the authentication device.

Figure 3:
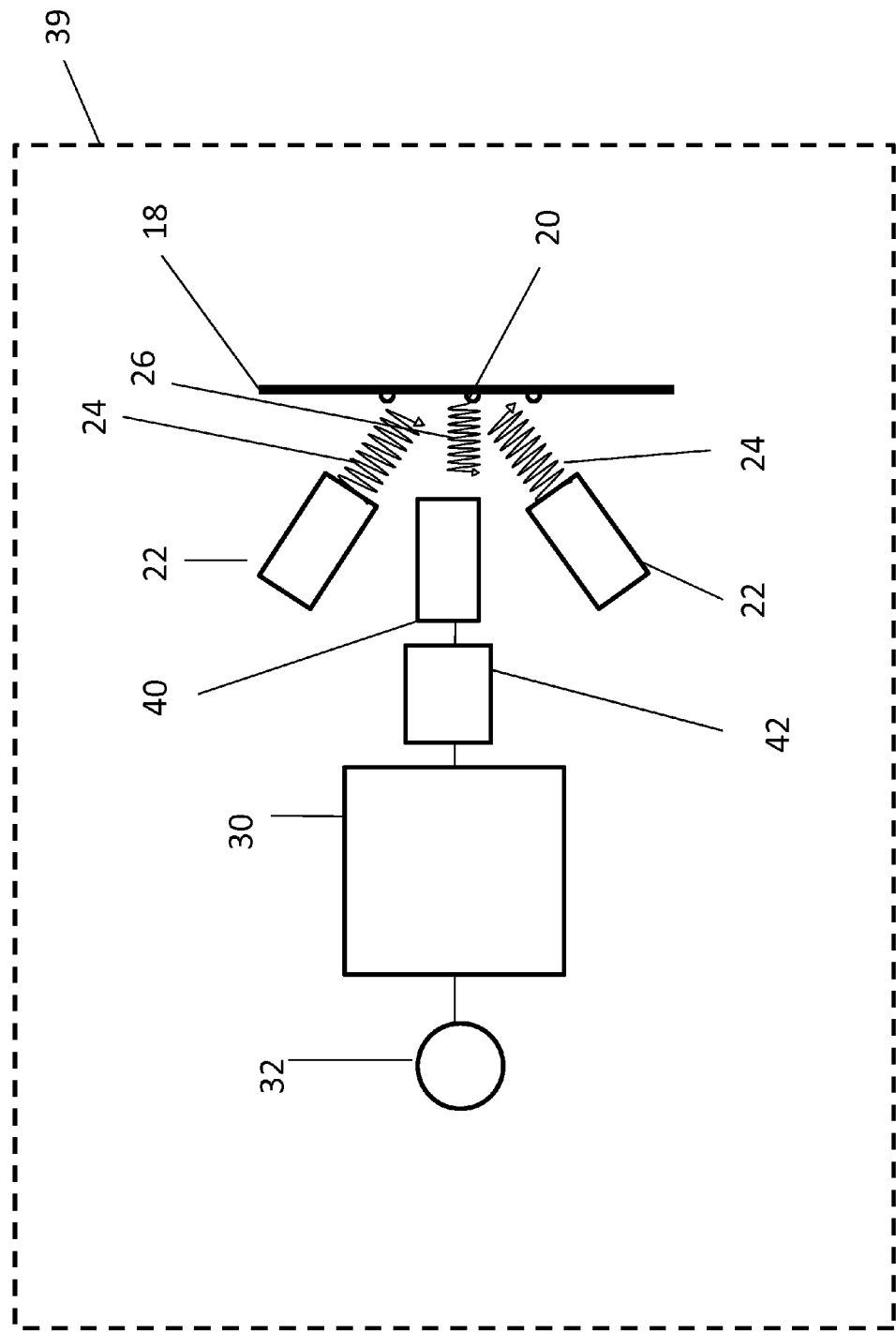
FIG. 3 shows a block diagram of a security marker detection system.

Referring to FIG. 3, a security marker detection system 39 is shown, which detects emission of security marker materials in a non image-wise fashion. One or more irradiation sources 22 direct electromagnetic radiation 24 towards the item to be authenticated 18. The electromagnetic radiation 24 can be in the ultraviolet, visible or infrared wavelength range. Typical wavelengths are 400 nm-700 nm for visible radiation, 200 nm-400 nm for ultraviolet radiation, and 700 nm-2500 nm for infrared radiation. Examples for irradiation sources are light emitting diodes (LED) or laser diodes (LD). The authentic item contains a random distribution of marker particles 20 either in an ink, in an overcoat varnish, or embedded in a substrate. The marker particles emit electromagnetic radiation 26 as a response to the radiation from the irradiation sources 22, which is detected by a photodetector 40 and amplified by an amplifier 42. A microprocessor 30 digitizes and analyzes the photodetector signal and determines a pass or fail indication which is displayed on the authentication indicator 32. Pass or fail indication can, for example, represent authentic and non-authentic, respectively.

Figure 4:
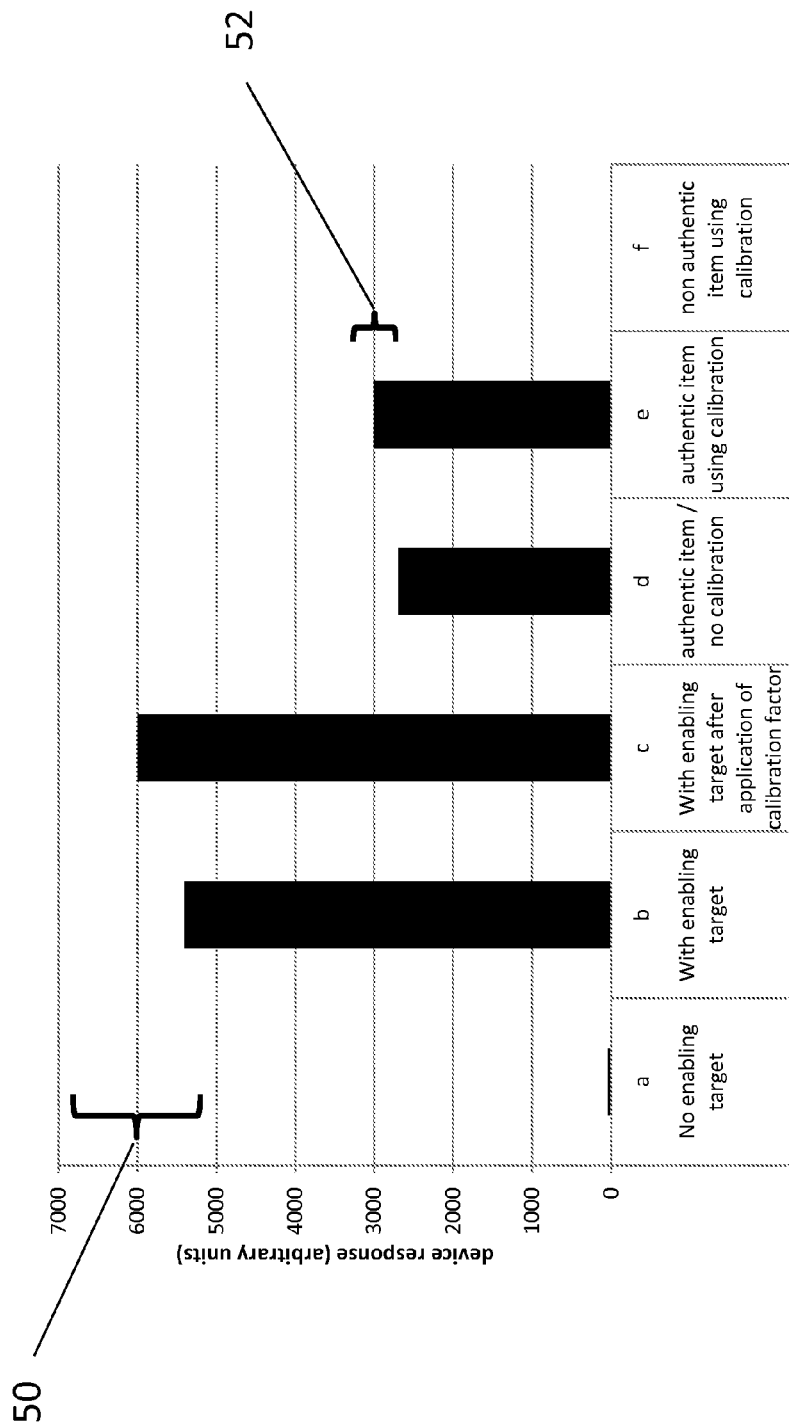
FIG. 4 shows an example of measurement results for the authentication device under different conditions.

FIG. 4 shows an example of measurement results of the device 10 under different conditions. In section a), the device was turned on in the absence of an enabling target. The device response, shown on the vertical axis is well outside the acceptance band for a genuine enabling target indicated by the bracket 50. Consequently, the device will remain in a disabled state allowing no further authentication processes to proceed. In section b), the enabling target was present while the device was turned on. The response is within the acceptance bracket 50 and, as a result, the device enters normal operational mode allowing subsequent authentication.

This measurement, however, also determines that the actual response value of 5400 was below the expected value of 6000, which is the center value of the acceptance band. As a result, the device will generate a calibration factor, in this case 1.111, which is applied to future reading. In the absence of other measurement variability, a subsequent power-on of the device placed on the enabling target will generate a response that exactly matches the expected value c).

The effect of the calibration on the authentication results is shown in sections d) and e) wherein the device is placed on an authentic item. In section d, no calibration is used and the response falls slightly outside the acceptance band for an authentic item 52. In this case the authentic item will be misidentified as non-authentic. However, when the calibration factor, 1.111 in this example, is used in section e), the response of the device is within the acceptance band for an authentic item and the item will correctly be identified as authentic. In the absence of a calibration procedure one would have to make the acceptance band for an authentic item wider, which reduces the selectivity of the authentication device. Section f) shows the response for a non-authentic item which is outside the acceptance band of the device leading to a fail indication.

The calibration process may incorporate a mathematical process such as multiplication of the device response with a calibration factor stored in the memory of microprocessor 30. It could also be a calibration factor that interacts with the characteristics of the irradiation source 22, photodetector 40 or amplifier 42 by, for example, increasing the current of the irradiation source or the amplifier gain when the response is below the expected value, or decreasing the current of the irradiation source or the amplifier gain when the response is above the expected value. Furthermore, while it is advantageous when calibration and authentication are conducted using the same optical components it is possible to design a system where the calibration and enabling step are conducted with optical components (e.g. illumination source or photodetector or both) that are different from the components used for the authentication process. In this case, different security marker particles could be involved in the calibration/enabling and authentication steps.

The invention has been described in detail with particular reference to certain preferred embodiments thereof, but it will be understood that variations and modifications can be effected within the scope of the invention.

PARTS LIST 10 security marker detection device (authentication device)
11 on/off switch
12 test button
14 authentication indicator pass
16 authentication indicator fail
17 enabling target
18 authentic item
20 security marker particle
22 irradiation source
24 exciting electromagnetic radiation
26 emitted electromagnetic radiation
30 microprocessor (memory)
32 authentication indicator
39 security marker detection system
40 photodetector
42 amplifier
50 bracket
52 authentic item

The invention claimed is:

1. A method of enabling an authenticating device comprising:
providing an item, a predetermined authentic item expected value, an enabling target, and a predetermined enabling target expected value;
measuring one or more enabling target attributes of the enabling target with the authenticating device;
comparing at least one measured enabling target attribute with the predetermined enabling target expected value;
if the at least one measured enabling target attribute matches the predetermined enabling target expected value, measuring an attribute of the item, comparing the measured item attribute with a predetermined item expected value, and authenticating the item if a match is determined and not authenticating the item if a match is not determined; and
if the at least one measured enabling target attribute does not match the predetermined enabling target expected value, indicating non-enablement of the authenticating device, and disabling the authenticating device.

2. The method of claim 1 wherein a record is created when at least one measured enabling target attribute does not match the predetermined enabling target expected value.

3. The method of claim 1 wherein the enabling target contains a material responsive to optical stimulation.

4. The method of claim 3 wherein the material is a fluorescent or phosphorescent marker coated on a substrate.

5. The method of claim 3 wherein the material is a fluorescent or phosphorescent marker contained within a polymer.

6. The method of claim 3 wherein the material is an ink containing a fluorescent or phosphorescent marker printed on a substrate.

7. The method of claim 3 wherein the material is impregnated in a substrate.

8. The method of claim 3 wherein the material in the enabling target is the same as material in an authenticating mark on an item or product.

9. The method of claim 3 wherein the material in the enabling target is different from material in an authenticating mark on an item or product.

10. The method of claim 1 wherein the measured enabling target attribute is an optical response to radiation emitted by the authenticating device.

11. The method of claim 10 wherein the radiation emitted by the authenticating device is infrared, visible, or ultraviolet.

12. The method of claim 10 wherein the radiation emitted by the authenticating device is generated by a light emitting diode (LED).

13. The method of claim 10 wherein the radiation emitted by the authenticating device is generated by a laser diode (LD).

14. The method of claim 1 wherein the measured attribute is a light intensity, a light frequency, or a combination of multiple frequencies.

15. The method of claim 1 wherein the measured enabling target attribute is a decay rate of a luminescence of a light-stimulated material.

16. The method of claim 1 wherein the predetermined enabling target expected value is a light intensity, light frequency, a combination of multiple frequencies, a light intensity range, a decay rate range, or a light frequency range.

17. The method of claim 1 wherein the authentication device is recalibrated when the measured enabling target attribute differs from the predetermined enabling target expected value by greater than one percent.

18. The method of claim 17 wherein a calibration factor is calculated by dividing the predetermined enabling target expected value by the measured enabling target attribute.

19. The method of claim 18 wherein the calibration factor is applied to recalibrate the authenticating device.

\* \* \* \* \*